United States Patent
Engelke et al.

(10) Patent No.: US 8,512,660 B2
(45) Date of Patent: Aug. 20, 2013

(54) METHOD AND DEVICE FOR THE ABSORPTIVE REMOVAL OF CARBON DIOXIDE FROM BIOGAS

(75) Inventors: Stephan Engelke, Maschen (DE); Uwe Jordan, Worpswede (DE)

(73) Assignee: MT-Biomethan GmbH, Zeven (DE)

( * ) Notice: Subject to any disclaimer, the term of this patent is extended or adjusted under 35 U.S.C. 154(b) by 0 days.

(21) Appl. No.: 13/616,041

(22) Filed: Sep. 14, 2012

(65) Prior Publication Data

US 2013/0071307 A1    Mar. 21, 2013

(30) Foreign Application Priority Data

Sep. 16, 2011   (EP) ..................... 11007558

(51) Int. Cl.
*C07C 7/00* (2006.01)
*C07C 7/10* (2006.01)
*C07C 7/11* (2006.01)
*B01D 53/14* (2006.01)
*B01D 53/62* (2006.01)
*B01D 53/72* (2006.01)
*B01D 19/00* (2006.01)
*B01J 10/00* (2006.01)

(52) U.S. Cl.
USPC ........... 423/220; 423/228; 423/232; 422/187; 95/183; 95/184; 96/216; 96/218; 585/240; 585/802

(58) Field of Classification Search
USPC ........... 423/220, 228, 232; 422/187; 95/183, 95/184; 96/216, 218; 585/240, 802
See application file for complete search history.

(56) References Cited

U.S. PATENT DOCUMENTS

| 2,811,219 | A | 10/1957 | Wenzl | |
|---|---|---|---|---|
| 2009/0156875 | A1* | 6/2009 | Tomioka et al. | 585/802 |
| 2010/0024647 | A1* | 2/2010 | Gunther | 95/183 |
| 2010/0036187 | A1* | 2/2010 | Gunther | 585/802 |
| 2011/0245572 | A1 | 10/2011 | Wolf et al. | |
| 2012/0097027 | A1* | 4/2012 | Gunther | 95/8 |
| 2012/0276616 | A1* | 11/2012 | Siegel et al. | 435/262 |

FOREIGN PATENT DOCUMENTS

| DE | 10 2005 051 952 | 12/2006 |
|---|---|---|
| DE | 10 2008 046 879 | 3/2010 |
| DE | 10 2009 013 883 | 3/2011 |
| DE | 10 2009 056 661 | 6/2011 |
| GB | 2 035 150 | 6/1980 |
| WO | 2008/000753 | 1/2008 |
| WO | 2008/034473 | 3/2008 |

OTHER PUBLICATIONS

European Search Report dated Feb. 6, 2012 in application No. EP 11 00 7558.

* cited by examiner

*Primary Examiner* — Timothy Vanoy
(74) *Attorney, Agent, or Firm* — Oblon, Spivak, McClelland, Maier & Neustadt, L.L.P.

(57) ABSTRACT

The absorptive removal of carbon dioxide from biogas using a scrubbing liquid in which carbon dioxide is chemically bound proceeds by heating the loaded scrubbing liquid, occurring after the absorption, to a temperature at which liberation of $CO_2$ begins. Immediately thereafter, the loaded scrubbing liquid is fed to at least one centrifugal separator for separating off the gas phase from the liquid phase, wherein methane and dissolved fractions of $CO_2$ escape via the gas phase. After separation is complete, the gas phase is passed into the absorber unit and the liquid phase is further heated to the temperature required for desorption and fed to the desorption unit for regeneration.

15 Claims, 2 Drawing Sheets

METHOD AND DEVICE FOR THE ABSORPTIVE REMOVAL OF CARBON DIOXIDE FROM BIOGAS

Figure 1:
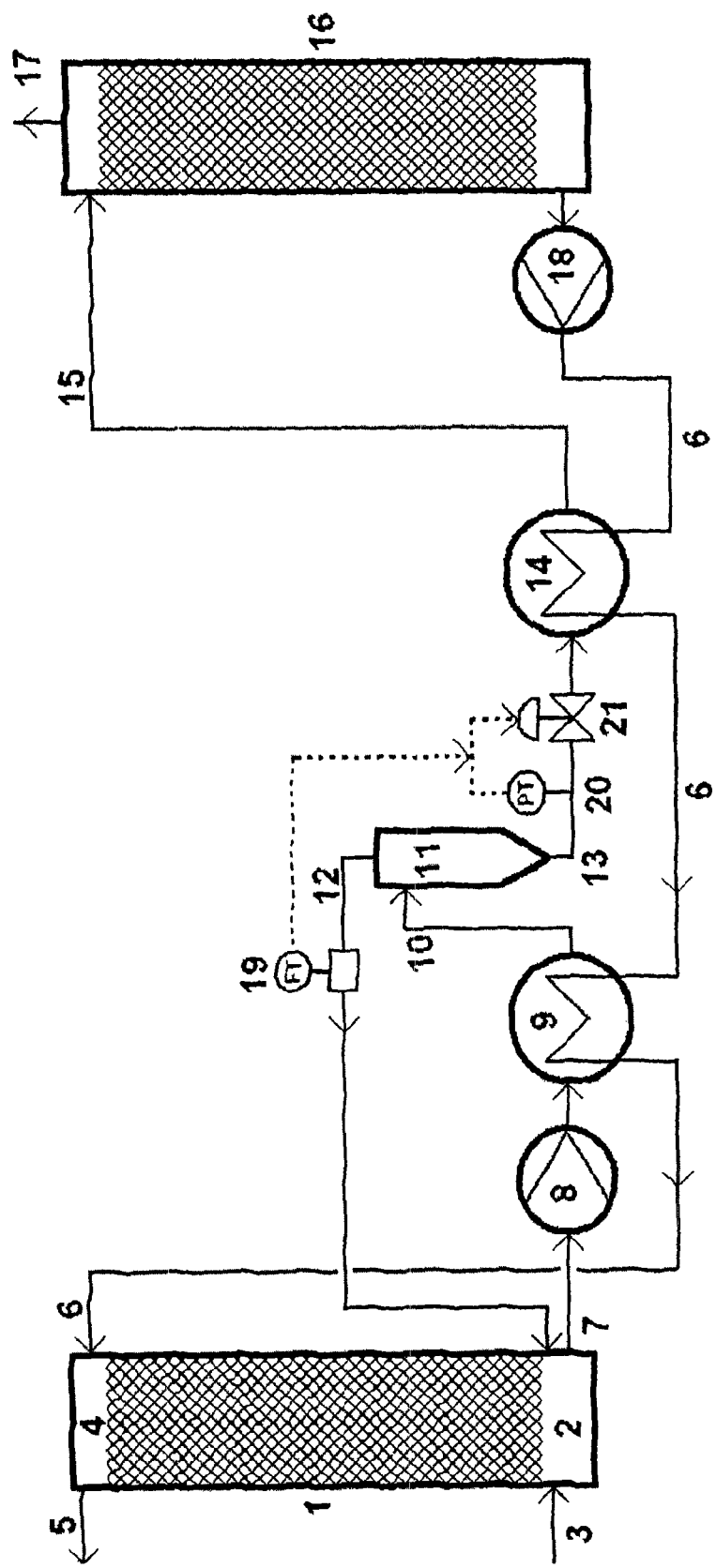

The invention relates to a method for the absorptive removal of carbon dioxide from biogas using a scrubbing liquid in which carbon dioxide is chemically bound, and to a device suitable for carrying out the method.

Biogas is a gas which is obtained from renewable raw materials or biological wastes. The main components of biogas are $CO_2$ and methane. If biogas is fed into a natural gas grid, $CO_2$ and other undesired byproducts must be removed therefrom.

For removing $CO_2$ from crude biogas, absorptive separation methods have achieved economic importance, in particular those methods which operate with scrubbing solutions or scrubbing liquids in which the gas component $CO_2$ is chemically bound. The advantage of these methods is that by chemisorption, a comparatively high loading of the scrubbing liquid can be achieved. Even in the case of chemisorption, relatively small amounts of gas are still physically bound. Owing to the high costs of the scrubbing liquid, it is necessary to regenerate the loaded scrubbing liquid. For this purpose, generally, a desorption stage is connected downstream of the absorption stage.

A method for the absorptive removal of carbon dioxide from biogas using amine-containing scrubbing liquid in which carbon dioxide is chemically bound is known, for example, from DE 10 2009 056 661 A1. For absorption, the scrubbing solution is passed in counterflow with the fed biogas through an absorber unit and the loaded scrubbing solution that is withdrawn is subsequently regenerated by desorption.

Off-gas produced during the desorption still contains residual amounts of methane that are termed what is known as methane slip.

A methane slip occurs in all known biogas separation methods and, depending on the separation method, can be up to 10% by volume.

The amount of methane gas that can be emitted in the off-gas of a biogas plant is restricted by law.

In order to meet these requirements, it is usual in practice to oxidize the off-gas thermally or catalytically. Possibly, further burnable gases must be added. The abovementioned oxidative treatment of the off-gas is connected with additional effort and is uneconomic.

In DE 10 2008 046 879 A1, it is proposed to pass the off-gas stream, before the oxidation, through storage vessels and/or fermentation residue stores that are designed to be closed, for inertization of the explosive gas concentrations forming there.

The substantial disadvantage, the loss of energy caused by the methane slip, however, cannot be eliminated by this solution.

The object of the invention is to provide a method for the absorptive removal of carbon dioxide from biogas, using a scrubbing liquid in which carbon dioxide is chemically bound, in which the loss of methane is decreased. In addition, a device suitable for carrying out the method is to be provided. The object is achieved according to the invention by the method features stated in claim 1. Advantageous developments of the procedure are subject matter of claims 2 to 10. A device suitable for carrying out the method is subject matter of claim 11. Dependent claims 12 to 15 relate to advantageous embodiments of the device.

The loaded scrubbing solution occurring after the absorption is heated to a temperature at which liberation of $CO_2$ begins. This temperature is dependent on the composition of the scrubbing liquid and the degree of loading of the scrubbing liquid. Surprisingly, it has been found in experiments that, in the case of exact maintenance of the temperature at which the liberation of $CO_2$ begins, effective separation only of methane from the loaded scrubbing solution succeeds. In the first 1 to 2% of liberated $CO_2$, virtually all of the residual amount of methane (methane slip) is contained. Subsequently, the loaded scrubbing solution is fed to at least one centrifugal separator for separating off the gas phase from the liquid phase, wherein methane and dissolved fractions of $CO_2$ escape via the gas phase. The gas phase separated off is passed into the absorber unit and flows through it together with the fed crude biogas.

The liquid phase separated off is further heated to the temperature necessary for desorption and fed to the desorption unit for regeneration.

Preferably, the loaded scrubbing liquid is heated to separation temperature in a first heat exchanger using regenerated scrubbing liquid fed in counterflow as heat carrier. This is energetically the most economic.

The loaded scrubbing liquid heated to separation temperature is, immediately after exit from the heat exchanger, introduced tangentially into the centrifugal separator.

The exact separation temperature is determined in advance in preliminary experiments in dependence on the loading of the scrubbing liquid.

The liquid phase removed from the centrifugal separator, a virtually methane-free $CO_2$-loaded scrubbing liquid, is passed through a second heat exchanger and heated therein to the required desorption temperature using regenerated scrubbing liquid fed in counterflow as heat carrier. Lastly, the loaded scrubbing solution is regenerated in the desorption unit and passed to the top of the absorption unit for use once more.

The $CO_2$ expelled from the scrubbing solution can be used, for example, for being introduced into greenhouses as gas or for the synthesis of organic or inorganic carbonaceous compounds.

Preferably, in the cyclone separator, the pressure of the gas phase is controlled, wherein temperature fluctuations in the centrifugal separator and changes in the loading of the scrubbing liquid that is fed can be compensated for by the pressure controller.

In the steady operating state, the pressure in the centrifugal separator is adjusted in such a manner that a predetermined amount of gas flows off and the pressure of the gas phase is altered accordingly in the event of a desired change in the amount of gas flowing off.

In the first heat exchanger, the temperature of the loaded scrubbing solution is monitored and the heat supply is controlled in dependence on the measured temperature. This process step is integrated in terms of control system into the central control of the biogas treatment plant.

As centrifugal separator, preferably a cyclone is used. Such a cyclone for a biogas treatment plant of medium size having a throughput of scrubbing liquid of approximately 10000 to 100000 l/h has a usable volume of approximately 8 to 140 liters (diameter of 100 to 300 mm, height 1000 to 2000 mm).

Depending on the amount of loaded scrubbing solution occurring after the absorption, instead of one cyclone, a plurality of generally smaller cyclones can be used that are operated either in series or parallel connection.

A particularly highly suitable scrubbing liquid is a scrubbing liquid that contains chemical substances that bind $CO_2$ in the form of carbonate or hydrogencarbonate, such as primary, secondary or tertiary amines, alkali metal salts of amino acids, alkali metal carbonate solutions, are used individually or as mixtures.

A device suitable for carrying out the method consists of an absorber unit having at least one absorber and a desorber unit having at least one desorber, wherein the sump of the absorber is connected to the desorber via a line bearing a loaded scrubbing liquid into which line at least one heat exchanger is incorporated. The desorber is connected to the top of the absorber via a line bearing purified scrubbing liquid.

After the first heat exchanger, at least one centrifugal separator is incorporated into the line bearing the loaded scrubbing liquid. The feed line opens out tangentially therein. Owing to the centrifugal force applied in the operating state, the gas phase that is separated off collects in the axis of rotation. The liquid phase is forced onto the inner wall of the centrifugal separator and flows off downwards.

At the top of the centrifugal separator, an off-gas line is arranged that opens out into the absorber below the absorber layer. The liquid line leading away from the centrifugal separator is connected to the top of the desorber, wherein a second heat exchanger is incorporated into the liquid line.

Preferably, in the bottom section of the centrifugal separator, a baffle plate is centrally arranged in such a manner that, between the wall of the centrifugal separator and the outer rim of the baffle plate, a narrow annular channel is formed as outlet opening for the liquid phase. Owing to the narrow annular channel, in the operating state, a bulge-like liquid backup forms which prevents any gas from co-escaping.

In the top section of the centrifugal separator, a submerged tube or riser tube is arranged that is connected to a float-controlled deaerating valve. In certain applications, it can also be expedient that a vacuum pump is further connected to the submerged tube or riser tube.

In the off-gas line of the centrifugal separator, a flow meter and a control valve are arranged, and in the line of the centrifugal separator leading away the liquid, a pressure sensor is arranged, which are interconnected via a control system.

Using the proposed solution, the methane slip may be virtually 100% eliminated. The methane liberated is fed together with the main gas stream of methane to an energetic utilization, e.g. feeding into the natural gas grid. The economic efficiency of the biogas plant is improved thereby, since the methane slip which otherwise is a loss, increases the yield of methane gas.

A further advantage is that during the use of scrubbing solutions, it is no longer necessary to pay attention to how high the methane slip thereof is. As a result, cheaper scrubbing media can also be used.

Figure 2:
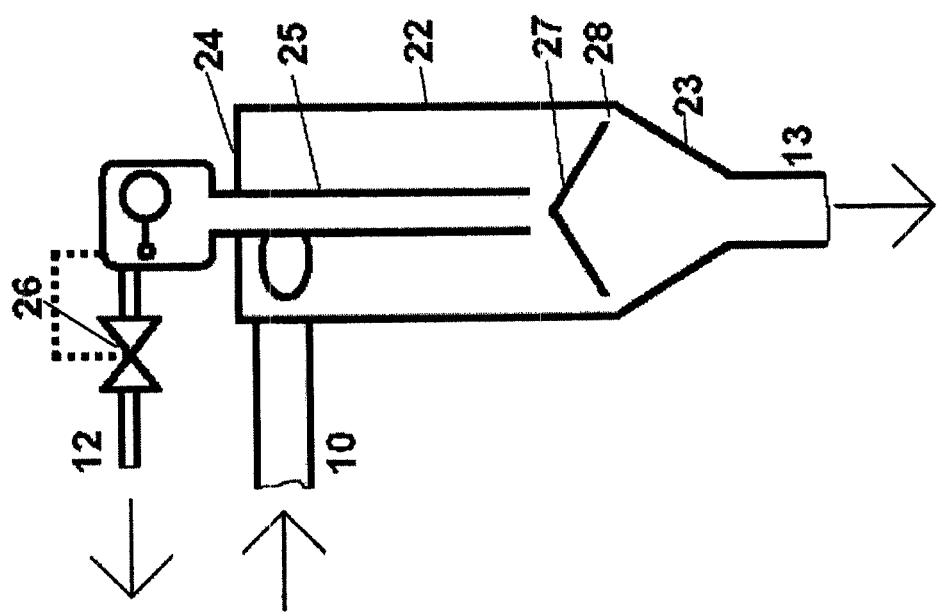

The invention will be described hereinafter with reference to an exemplary embodiment. In the associated drawing:

FIG. 1 shows a device according to the invention in simplified schematic view and FIG. 2 shows a cyclone as a single component in a simplified cross sectional view.

The device shown in FIG. 1 consists of the assemblies absorber 1, first heat exchanger 9, cyclone 11, second heat exchanger 14 and desorber 16.

The absorber 1 is connected in the bottom section 2 (sump) to a line 3 for the biogas to be purified (crude gas). The purified biogas (methane) is removed in the top section 4 (at the top) via a line 5. The scrubbing liquid fed via the line 6 is finely distributed in the absorber 1. The crude biogas is passed in counterflow to the scrubbing liquid through the absorption column 1.

At a temperature of approximately 40° C. the scrubbing liquid, e.g. an amine solution, absorbs the carbon dioxide present in the biogas. The purified biogas (methane) is withdrawn at the top of the absorption column 1. In the sump 2 of the absorber 1, via a line 7 into which a first pump 8 is incorporated, the loaded scrubbing liquid is pumped off and fed to a first heat exchanger 9. In the heat exchanger 9, the loaded scrubbing liquid is heated using regenerated scrubbing liquid as heat carrier to the required separation temperature. When this is reached, in the first heat exchanger 9, liberation of $CO_2$ begins. This is the point in time at which the loaded scrubbing liquid is pumped via the line 10 at a defined pressure into the cyclone 11. Surprisingly, it has been found that in the first 1 to 2% of liberated $CO_2$, virtually up to 100% of the methane slip is already present. Accordingly, the heating of the loaded scrubbing liquid must be terminated at this temperature and said scrubbing liquid must be fed to the cyclone 11 for separation of the gas phase from the liquid phase. The feed into the cyclone 11 proceeds tangentially in the top section. The structure of the cyclone will be considered in even more detail hereinafter. In the cyclone 11, the loaded scrubbing liquid that is fed is separated into a methane-rich gas phase and a virtually methane-free liquid phase. The gas phase is withdrawn at the top of the cyclone 11 via a line 12 and passed into the absorber 1 at the bottom section 2, where it ascends together with the fed crude biogas. The loaded scrubbing liquid occurring at the conical outlet of the cyclone 11 is pumped off via a line 13 and fed to a second heat exchanger 14 for heating to desorption temperature. In the second heat exchanger 14, the loaded scrubbing liquid is heated to the required temperature using regenerated scrubbing liquid as heat carrier and introduced via the line 15 into the desorption column 16 at the top thereof at elevated pressure and then expanded. The desorption can also proceed via a multistage expansion in a manner known per se. Owing to the expansion, the $CO_2$ bound in the scrubbing liquid escapes. The gas mixture ($CO_2$, water and sulfur compounds) occurring is taken off as vapors via a line 17 arranged at the top of the desorption column 16 and can be used as heat carrier and subsequently further treated.

The regenerated scrubbing liquid occurring at the sump of the desorption column 16 having a temperature of approximately 120 to 150° C. is utilized as heat carrier and pumped via the line 6, into which a second pump 18 is incorporated, through the second heat exchanger 14 and then through the first heat exchanger 9 and in the process cooled to approximately 40 to 50° C. and is fed to the absorber 1.

The loaded scrubbing liquid can be separated into a gas phase and a liquid phase by means of a controlled or uncontrolled centrifugal separator. In FIG. 1, one embodiment variant is shown having a controlled cyclone 11.

In the case of an uncontrolled centrifugal separator or cyclone, a change in the operating state such as, for example, a change in the amount of $CO_2$ absorbed in the absorber unit 1, can only be compensated for by changing the temperatures in the absorber 1 and desorber 16. However, narrow limits are imposed on this measure by the aforesaid operating profile of the biogas treatment plant.

The gas stream that is separated off in the cyclone 11 and removed by the line 12 can be controlled by a pressure controller. For the pressure control a flow meter 19 is incorporated into the off-gas line 12 and a pressure sensor 20 and a control valve 21 are incorporated into the line 13 attached at the cyclone exit. These are interconnected via control system, which is indicated by the dashed line.

If the pressure in the cyclone 11 is increased, then the outgassing at the intake into the cyclone 11 starts at a higher temperature. Via the pressure control in cyclone 11, changes in the temperature in cyclone 11 can be compensated for. A control range of the pressure from 2 to 8 bar makes it possible to compensate for temperature fluctuations over a range of up to 20 K.

In addition, using the pressure controller, it is possible to react to changes in the loading state of the scrubbing solution. If the pressure in the cyclone is increased, it is possible to separate off virtually the entire amount of methane from a more highly loaded scrubbing solution in the cyclone 11. If, in contrast, the pressure in the cyclone is decreased, a less loaded scrubbing solution in cyclone 11 can be treated. For a control range from 3 to 6 bar, loading fluctuations can be compensated for over a range of up to 20 g/l.

With regard to control, in the operating state a procedure is followed such that as required value, a preset defined amount of gas flows from the cyclone. If the amount of gas flowing off is to be increased, the pressure in the cyclone is decreased. For decreasing the amount of gas, the pressure in the cyclone is increased.

The cyclone 11 used is shown as a single component in FIG. 2 in an enlarged view.

The cyclone 11 consists of stainless steel and has a diameter of 200 mm and a height of 1500 mm. The cylindrical section 22 has a length or height of 750 mm. In the bottom section, the cyclone 11 has a conical outlet 23, to which the line 13 is attached. At the top ends of the cyclone 11, a cover 24 is arranged. This has a central opening into which a submerged tube 25 is inserted which projects downwards into the cyclone 11 and is arranged in the axis of rotation of the cyclone 11. In the submerged tube 25, the gas bubbles formed during the separation process ascend. At the end standing out at the top of the submerged tube 25 a float-controlled deaerating valve 26 is arranged which is not shown conjointly in FIG. 1.

This has the effect that only the gaseous substances can leave the cyclone 11 via the line 12.

In the lower region of the cyclone 11, a conical baffle plate 27 is arranged, the point of which points upwards. The baffle plate 27 extends radially outwards to the extent that only a narrow annular channel 28 is formed. This ensures that only liquid can flow off and no gas bubbles.

EXAMPLE 1

As scrubbing solution for absorption of the fed biogas (crude gas), a commercially conventional aqueous solution of MDEA and piperazine is used, having concentrations of 3.5 mol/l of MDEA and 0.5 mol/l of piperazine. The scrubbing solution, after the absorption, has a temperature of 50° C. The loadings with carbon dioxide and methane are 45 g/l and 0.07 g/l (methane slip), respectively.

The loaded scrubbing solution is heated to a temperature of 112° C. in the first heat exchanger 9 at a pressure of 6 bar. When this temperature is reached, the loaded scrubbing solution is introduced tangentially into the cyclone 11.

Under these conditions, shortly before introduction into the cyclone 11, a gas phase forms having the following composition: $CO_2$: 72.5% by volume; $CH_4$: 6.5% by volume; steam: 21% by volume.

The loading of the liquid phase with carbon dioxide is 44.8 g/l. The loading of the liquid phase with methane is 0.0014 g/l.

98% of the methane and only 0.4% of the carbon dioxide pass into the gas phase. In the cyclone 11, the gas phase is separated off from the liquid phase and passed to the biogas stream via the line 12 into the absorber 1.

EXAMPLE 2

The composition of the scrubbing solution used is the same as in example 1.

After exit from the absorber 1, the loading of the scrubbing solution with carbon dioxide is 40 g/l. The scrubbing solution is heated to 112° C. in the first heat exchanger under the same conditions as in example 1. The gas phase forming under these conditions has the following composition: 20.4% by volume methane, 60.6% by volume $CO_2$ and 21% by volume steam. In the liquid phase, 0.055 g/l of methane are further dissolved. Therefore only 22% of the methane has passed over into the gas phase.

In order to achieve a methane slip as low as possible, the pressure in the cyclone 11 is reduced to 5.1 bar. The temperature of 112° C. remains virtually constant. As a result of the lowered pressure, larger amounts of methane and carbon dioxide pass over into the gas phase. This consists of 14% by volume methane, 63.1% by volume $CO_2$ and 22.8% by volume steam.

In the liquid phase a further 0.008 g/l of methane are dissolved. 88% of the methane pass over into the gas phase. The gas phase is separated off from the liquid phase in the cyclone and passes into the absorber 1.

EXAMPLE 3

A similar procedure as in example 1 is followed, but with the only difference that the temperature of the scrubbing solution after the absorption is 60° C. In the first heat exchanger, the loaded scrubbing solution must be heated to a temperature of 117° C. in order then to be able to pump it into the cyclone 11. At this temperature, a gas phase forms having the following composition: 0.2% by volume methane, 77% by volume $CO_2$ and 22.7% by volume steam.

The liquid phase does not contain any methane, but contains 38.8 g/l of $CO_2$ in dissolved form.

Under these conditions, in the event of separation of the gas phase from the liquid phase in a centrifugal separator, much too much $CO_2$ would be separated off conjointly, and circulated, which would be uneconomic.

This is excluded by increasing the pressure in the cyclone to 7.5 bar. As a result, less $CO_2$ passes over into the gas phase.

The gas phase forming under these conditions contains 10.8% by volume methane, 70.6% by volume $CO_2$ and 18.6% by volume steam. In the liquid phase, 0.0068 g/l of methane and 44.89 g/l of $CO_2$ remain. Therefore, more than 90% of the methane pass over into the gas phase. The methane-rich gas phase exiting from the cyclone 11 passes into the absorber 1.

The examples verify that, using the proposed procedure, in the regeneration of a loaded scrubbing liquid, the methane slip can be decreased by approximately 90 to 98%.

REFERENCE SIGNS

1 Absorber
2 Bottom section (sump) of 1
3 Biogas line
4 Top section (top) of 1
5 Methane line
6 Regen. scrubbing liquid line
7 Loaded scrubbing liquid line
8 Pump
9 First heat exchanger
10 Line
11 Cyclone
12 Vapor line
13 Scrubbing liquid line
14 Heat exchanger
15 Scrubbing liquid line
16 Desorption column 17 Vapor line
18 Pump
19 Flow meter
20 Pressure sensor
21 Control valve
22 Cylindrical section
23 Conical outlet
24 Cover
25 Submerged tube
26 Deaerating valve
27 Baffle plate
28 Annular channel

The invention claimed is:

1. A method for the absorptive removal of carbon dioxide from biogas comprising using a scrubbing liquid in which carbon dioxide is chemically bound, wherein the scrubbing solution, for absorption, is passed in counterflow with the fed biogas through an absorber unit (1) and the loaded scrubbing liquid that is withdrawn is regenerated by desorption, which comprises heating the loaded scrubbing liquid occurring after the absorption to a temperature at which liberation of $CO_2$ begins, and immediately thereafter feeding the loaded scrubbing liquid to at least one centrifugal separator (11) for separating off the gas phase from the liquid phase, wherein methane and dissolved fractions of $CO_2$ escape via the gas phase, and after separation is complete, passing the gas phase into the absorber unit (1) and heating the liquid phase further to the temperature necessary for desorption, and feeding it to the desorption unit (16) for regeneration.

2. The method according to claim 1, wherein the loaded scrubbing liquid that is withdrawn is passed after the absorption through a first heat exchanger (9) and heated therein to the required separation temperature using regenerated scrubbing liquid fed in counterflow as heat carrier, and subsequently introduced tangentially into the centrifugal separator (11).

3. The method according to claim 1, wherein the liquid phase removed from the centrifugal separator (11) is passed through a second heat exchanger (14) and heated therein to the required desorption temperature using regenerated scrubbing liquid fed in counterflow as heat carrier, and subsequently passes into the desorption unit (16).

4. The method according to claim 1, wherein the pressure of the gas phase in the cyclone separator is controlled, wherein temperature fluctuations in the centrifugal separator (11) and changes in the loading of the scrubbing liquid that is fed can be compensated for by the pressure controller.

5. The method according to claim 1, wherein, in the steady operating state, the pressure in the centrifugal separator (11) is adjusted in such a manner that a predetermined amount of gas flows off and the pressure is altered in the event of a desired change in the amount of gas flowing off.

6. The method according to claim 2, wherein, in the first heat exchanger (9), the temperature of the loaded scrubbing solution is monitored and the heat supply is controlled in dependence on the measured temperature.

7. The method according to claim 1, wherein, as centrifugal separator, a cyclone (11) is used.

8. The method according to claim 1, wherein, instead of one cyclone (11), a plurality of cyclones are used that are operated either in series or parallel connection.

9. The method according to claim 1, wherein a scrubbing liquid is used that contains chemical substances that bind $CO_2$ in the form of carbonate or hydrogencarbonate.

10. The method according to claim 9, wherein, as chemical substances, primary, secondary or tertiary amines, alkali metal salts of amino acids, alkali metal carbonate solutions, are used individually or as mixtures.

11. A device for carrying out an absorptive removal of carbon dioxide from biogas comprising:
an absorber unit having at least one absorber (1) and a desorber unit having at least one desorber (16), wherein the bottom section (2) of the absorber (1) is connected via a line (7) bearing a loaded scrubbing liquid, into which line at least one heat exchanger is incorporated, is connected to the desorber (16), and from the desorber (16), a line (6) bearing purified scrubbing liquid leads to the top of the absorber (1), which comprises, downstream of the first heat exchanger (9) at least one centrifugal separator (11) is incorporated into the line (7) bearing the loaded scrubbing liquid, wherein the feed line (10) into the centrifugal separator (11) opens out tangentially therein, at the top of the centrifugal separator (11), an off-gas line (12) is arranged which leads to the bottom section (2) of the absorber (1), and the liquid line (13) leading away from the centrifugal separator (11) is connected to the top of the desorber (16), wherein a second heat exchanger (14) is incorporated therein.

12. The device according to claim 11, wherein, as centrifugal separator, a single cyclone (11) or a plurality of series- or parallel-connected cyclones are arranged.

13. The device according to claim 11, wherein, in the bottom section of the centrifugal separator (11), a baffle plate (27) is centrally arranged in such a manner that, between the wall of the centrifugal separator (11) and the outer rim of the baffle plate (27), a narrow annular channel (28) is formed as outlet opening for the liquid phase.

14. The device according to claim 11, wherein, in the top section of the centrifugal separator (11), a submerged tube (25) is arranged that is connected to a float-controlled deaerating valve (26) and optionally to a vacuum pump.

15. The device according to claim 11, wherein, in the off-gas line (12) of the centrifugal separator (11), a flow meter (19) is arranged, and in the line (13) of the centrifugal separator (11) leading away the liquid, a pressure sensor (20) and a control valve (21) are arranged, which are interconnected via a control system.

* * * * *